United States Patent
Ogura et al.

(10) Patent No.: US 8,047,734 B2
(45) Date of Patent: Nov. 1, 2011

(54) PENCIL-FORM COSMETIC COMPOSITION AND COSMETIC PRODUCT THEREOF

(75) Inventors: Yuuki Ogura, Yokohama (JP); Kiyoshi Kawada, Yokohama (JP); Takashi Minami, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 0 days.

(21) Appl. No.: 12/994,240

(22) PCT Filed: Nov. 11, 2009

(86) PCT No.: PCT/JP2009/069520
§ 371 (c)(1),
(2), (4) Date: Nov. 23, 2010

(87) PCT Pub. No.: WO2010/055954
PCT Pub. Date: May 20, 2010

(65) Prior Publication Data
US 2011/0061676 A1   Mar. 17, 2011

(30) Foreign Application Priority Data
Nov. 11, 2008 (JP) .................................. 2008-288712

(51) Int. Cl.
B43K 19/00 (2006.01)
(52) U.S. Cl. .................. 401/49; 424/63; 424/401
(58) Field of Classification Search .............. 401/52, 401/92, 93, 94, 96, 97; 424/61, 63, 64, 401
See application file for complete search history.

(56) References Cited

U.S. PATENT DOCUMENTS

| | | | | |
|---|---|---|---|---|
| 5,650,139 A | * | 7/1997 | Nojima | 424/64 |
| 6,471,951 B1 | * | 10/2002 | Nardolillo et al. | 424/63 |
| 2005/0069508 A1 | | 3/2005 | Pays et al. | |

FOREIGN PATENT DOCUMENTS

| | | |
|---|---|---|
| JP | 2001-226223 | 8/2001 |
| JP | 2005-53915 | 3/2005 |
| JP | 2006-176422 | 7/2006 |
| JP | 2007-210958 | 8/2007 |
| JP | 2008-143800 | 6/2008 |
| JP | 2008-156245 | 7/2008 |

OTHER PUBLICATIONS

Japanese Patent Abstract for Publication No. 2001-226223 published Aug. 21, 2001, eight pages.
Japanese Patent Abstract for Publication No. 2006-176422 published Jul. 6, 2006, nine pages.
Japanese Patent Abstract for Publication No. 2007-210958 published Aug. 23, 2007, nine pages.
Japanese Patent Abstract for Publication No. 2008-143800 published Jun. 26, 2008, ten pages.
Japanese Patent Abstract for Publication No. 2008-156245 published Jul. 10, 2008, nine pages.
International Search Report for corresponding PCT/JP2009/069520 mailed Feb. 16, 2010, three pages.
Takeo Mitsui, "Shin Keshohingaku," New Cosmetic Sciences, 2nd Edition, Jan. 18, 2001, pp. 417-418 and partial translation, one page.

* cited by examiner

*Primary Examiner* — David Walczak
(74) *Attorney, Agent, or Firm* — Rankin, Hill & Clark LLP

(57) ABSTRACT

A pencil-form cosmetic composition which has a good stability at high temperature, an excellent smoothness during application, and an excellent long-lasting property, and also provides a cosmetic product thereof. The pencil-form cosmetic composition comprises (a) 15 to 50% by mass of volatile oil, (b) 5 to 25% by mass of heavy liquid isoparaffin, and (c) 5 to 30% by mass of rice wax.

2 Claims, No Drawings

PENCIL-FORM COSMETIC COMPOSITION AND COSMETIC PRODUCT THEREOF

FIELD OF THE INVENTION

This invention relates to a pencil-form cosmetic composition and cosmetic products thereof, and in particular, relates to a pencil-form cosmetic composition which is excellent in the long-lasting property and the smoothness during application, and to cosmetic products thereof.

BACKGROUND OF THE INVENTION

Generally, a long-lasting pencil-form cosmetic composition, such as a lipliner pencil and an eyebrow pencil, is mainly comprised of solid oils, liquid oils, volatile oils, and resins. When such a cosmetic composition is applied to the skin, a continuous film is formed on the skin after vaporization of the volatile oils in the formulation. Since the formed film is water-insoluble, the cosmetic composition has no bleeding owing to sweat or tears, resists on sebum, and can be removed just by being wetted with a makeup remover. For this type of pencil-form cosmetic composition, the selection of resin is important in terms of its usability. An organic silicone resin (e.g., a 50% solution of trimethylsiloxysilicate in 50% decamethylcyclopentasiloxane), which was recently developed, is widely used because a pencil-form cosmetic composition using the resin has good water resistance and oil resistance as well as an excellent long-lasting property (e.g., see Patent Literature 1).

Pencil-form cosmetic compositions, such as eyeliner pencils, eyebrow pencils, and lip pencils, have some types of products: one type includes those used by sharpening like a lead pencil; and another type includes those used by advancing like a mechanical pencil. Further, the advance type includes those having a refillable core like a cartridge.

Since these pencil-form cosmetic compositions are used by being directly applied to eyes and lips, it is preferred that it has smoothness during application in addition to long lasting property. However, conventional pencil-form cosmetic compositions could not always satisfy these needs.

There have been some attempts to improve long-lasting property or provide smoothness by incorporating volatile oil agents into pencil-form cosmetic compositions. In Patent Literature 2, a stick cosmetic composition incorporating an organic silicone resin, a volatile oil agent, a heavy liquid isoparaffin, a lipophilic gelling agent, and powder has been developed.

However, this stick cosmetic composition has a disadvantage in lacking the stability because a volatile oil agent, especially a hydrocarbon volatile oil agent which is highly effective in long-lasting property or smoothness, vaporizes at high temperature.

Patent Literature 1: Japanese Unexamined Patent Publication No. 2007-21 0958
Patent Literature 2: Japanese Patent No. 3654808

DISCLOSURE OF THE INVENTION

Problem to be Solved by the Invention

The object of the present invention is to provide a pencil-form cosmetic composition which has a good stability at high temperature, an excellent long-lasting property, and an excellent smoothness during application, and it is also to provide cosmetic products thereof.

Means to Solve the Problem

The present inventors have initially focused on the fact that whether volatile oils vaporize easily or not depends on combination of oils and waxes. As a result, they found that the incorporation of specific amounts of volatile oil, heavy liquid isoparaffin, and rice wax inhibits the volatile oil from vaporizing, thus leading to obtaining a pencil-form cosmetic composition which has a good stability, an excellent long-lasting property, and an excellent smoothness during application.

The present invention provides a pencil-form cosmetic composition comprising (a) 15 to 50% by mass of volatile oil, (b) 5 to 25% by mass of heavy liquid isoparaffin, and (c) 5 to 30% by mass of rice wax.

The present invention also provides a cosmetic product wherein the pencil-form cosmetic composition is contained in a mechanical pencil-shaped container which enables the pencil-form cosmetic composition to advance.

Effect of the Invention

The cosmetic composition of the present invention has a good stability at high temperature, an excellent smoothness during application, and an excellent long-lasting property.

Also, in the cosmetic product of the present invention, as the pencil-form cosmetic composition is contained in the mechanical pencil-shaped container which enables the pencil-form cosmetic composition to advance, the vaporization of volatile oil is more inhibited. Thus, the pencil-form cosmetic composition can be applied stably and smoothly in an easy way, resulting in a good usability.

BEST MODE FOR CARRYING OUT THE INVENTION

Hereinafter, best mode for carrying out the present invention is described.

In the present invention, the incorporation of rice wax inhibits volatile oils, especially hydrocarbon volatile oils, from vaporizing at high temperature, and a smooth feeling in use during application can be stably provided. In addition, the incorporation of heavy liquid isoparaffin provides an excellent long-lasting property because a film of rice wax and heavy liquid isoparaffin remains after the vaporization of volatile oil. As a result, the pencil-form cosmetic composition having not only long-lasing property but also a smooth feeling during application can be obtained.

Examples of the volatile oil (a) used in the present invention include silicone oils such as decamethylcyclopentasiloxane, polymethylcyclohexasiloxane, and polymethylcyclotetrasiloxane; and hydrocarbon oils such as isododecane, isohexadecane, and isoparaffin (C10 to 14). Among them, hydrocarbon oils such as isoparaffin (C10 to 14) are preferably used. Hydrocarbon oils are highly effective in providing long-lasting property and smoothness. Most preferably, decamethylcyclopentasiloxane and isoparaffin are used in combination as volatile oils.

The amount of volatile oil (a) is 15 to 50% by mass, more preferably 20 to 40% by mass with respect to the total amount of the pencil-form cosmetic composition. When the amount of component (a) is too large, the vaporized amount becomes large to deteriorate the stability. When it is too small, the amount of involatile oil becomes large accordingly to deteriorate the long-lasting property. When decamethylcyclopentasiloxane and isoparaffin are used in combination, it is preferred that the amounts are respectively 10 to 25% by mass.

Next, the heavy liquid isoparaffin (b) is explained.

The heavy liquid isoparaffin (b) is polyisobutene having 10000 to 500000 cps viscosity. After the vaporization of volatile oil, the heavy liquid isoparaffin forms a film together with rice wax, and this film makes the long-lasting property better.

The amount of heavy liquid isoparaffin (b) is 5 to 25% by mass, more preferably 10 to 20% by mass with respect to the total amount of the pencil-form cosmetic composition. The component (b) helps the film to be maintained after the vaporization of volatile oil. However, when the amount of component (b) is too large, the relative amount of solidifying agent in the film after the vaporization of volatile oil becomes small to deteriorate the long-lasting property. When it is too small, the stretch property of film is deteriorated.

The rice wax (c) used in the present invention is prepared by purifying waxy oil separated during purification of rice oil extracted from rice bran. Among various waxes, the use of rice wax inhibits hydrocarbon volatile oils from vaporizing at high temperature to achieve a good stability at high temperature.

The amount of rice wax (c) is 5 to 30% by mass, more preferably 12 to 25% by mass with respect to the total amount of the pencil-form cosmetic composition. When the amount of component (c) is too large, the cosmetic composition lacks smoothness. When it is too small, the long-lasting property, formability, or stability becomes poor.

In the present invention, the following components can be used in addition to the above-mentioned oils used as essential components: solid fats such as Japan wax, cacao butter, hydrogenated castor oil, hydrogenated oil, palm oil, hydrogenated coconut oil, and Japan wax kernel oil; waxes such as carnauba wax, beeswax, candelilla wax, jojoba wax, lanolin, and shellac wax; hydrocarbon waxes such as polyethylene wax, paraffin wax, ceresin, and microcrystalline wax; higher alcohols such as behenyl alcohol, cetanol, and batyl alcohol; solid oils such as silicone wax; and liquid oils such as cetyl 2-ethylhexanoate, glyceryl triisostearate, neopentylglycol dicaprate, diester of isostearyl alcohol and malic acid, trimethylolpropane triisooctanoate, triglyceride isooctanoate, pentaerythritol tetraisooctanoate, octyl palmitate, acetyl tributyl citrate, dimethylpolysiloxane (6 to 5000 cs), and methylphenylpolysiloxane.

In the present invention, color agents are incorporated in addition to the above-mentioned essential components. Any coloring agents can be used as long as they are generally used in pencil-form cosmetic compositions, and they may be in the form of powder or lake (the form in which oils are kneaded). The coloring agents may be inorganic pigments, organic pigments, or pearlescent agents. The amount of coloring agents is preferably 5 to 40% by mass with respect to the pencil-form cosmetic composition.

In the pencil-form cosmetic composition of the present invention, pigments, moisturizers, preservatives, antioxidants, perfumes drugs, solvents, and so on can be used in addition to the above-mentioned components, as needed, within a qualitative/quantitative range that does not undermine the effects of the present invention.

In addition to lipliner pencils, eyeliner pencils, and eyebrow pencils, the pencil-form cosmetic composition of the present invention can be used in lipsticks, pencil-form eye shadows, and so on. Examples of the product form include a lead pencil type and a mechanical-pencil type. In particular, an advancing mechanical-pencil type is preferred.

According to the present invention, the cosmetic product wherein the pencil core-shaped cosmetic composition is put in the mechanical pencil-shaped container which enables the cosmetic composition to advance is provided.

EXAMPLES

Hereinafter, the present invention will be further illustrated in the following examples. However, the present invention should not be limited by these examples in any manner. Unless otherwise noted, the amount of each component is expressed in mass %.

Prior to explaining the examples, the method of testing the effects used in the present invention will be explained.

(1) Evaluation Test for Long-Lasting Property and Smoothness

Ten panels used each sample and rated it on the following seven point scale for the long-lasting property after application and the smoothness during application. The average score for each sample was calculated from the total score of ten panels and evaluated according to the following four-grade criteria.

6: Very good
5: Good
4: Slightly good
3: Normal
2: Slightly bad
1: Bad
0: Very bad
(Four-Grade Criteria)
5.2 or more: ⊚ (Very good)
3.2 or more to less than 5.2: O (Good)
1.2 or more to less than 3.2: Δ (Neither good nor bad or slightly bad)
Less than 1.2: X (Bad)

(2) Test for Stability in Volatilization

The content of a lipliner pencil prepared in the following method was filled in a gastight container for a foundation at 80° C., and it was left at 50° C. with closed cover. After four weeks, the decreased weight was measured. In the criteria, the vaporization amount means the measured decreased weight.
(Criteria)
O: The vaporization amount is 10% by mass or less.
X: The vaporization amount exceeds 10% by mass.

(3) Test for Dispersibility

The content of a lipliner pencil prepared in the following method was filled in a gastight container for a foundation at 80° C., and it was left to stand still. After one day, the dispersibility of each sample in a solidified state was visually evaluated.
(Criteria)
O: The surface is in a homogeneous state.
Δ: The surface is partly inhomogeneous in a patchy and/or punctate state.
X: The surface is wholly inhomogeneous in a patchy and/or punctate state.

Test Examples 1 to 6

Lipliner Pencils

The raw materials shown in Table 1 except volatile oils were kneaded, dissolved at 100° C., and mixed with stirring. Then volatile oils were added thereto, and the mixture was mixed by stirring at 80° C. and filled in a container to mold a pencil core. The size of pencil core was ø3×250 (mm), and the pencil core was cut appropriately so as to fit into a container. The pencil core was set, as an advancing core, in an advancing mechanical pencil-shaped container to prepare the lipliner pencil.

Each of the obtained lipliner pencils of Test Examples 1 to 6 was evaluated for the stability in volatilization and the dispersibility according to the above-mentioned criteria. The result is shown in Table 1.

TABLE 1

| (Lipliner pencil) | Test Example 1 | Test Example 2 | Test Example 3 | Test Example 4 | Test Example 5 | Test Example 6 |
|---|---|---|---|---|---|---|
| Polyethylene | — | — | 20 | — | — | — |
| Paraffin wax | — | — | — | 20 | — | — |
| Rice wax | 20 | 20 | — | — | 20 | — |
| Candelilla wax | — | — | — | — | — | 20 |
| Hydrogenated polyisobutene | 10 | 10 | 10 | 10 | 10 | 10 |
| Sorbitan sesquiisostearate | 1 | 1 | 1 | 1 | 1 | 1 |
| Decamethylcyclopentasiloxane | 50 | 25 | — | — | — | — |
| Isododecane | — | 25 | 50 | 50 | 50 | 50 |
| Powder (coloring agents) | 19 | 19 | 19 | 19 | 19 | 19 |
| Total (%) | 100 | 100 | 100 | 100 | 100 | 100 |
| Stability in volatilization | ◯ | ◯ | X | X | ◯ | ◯ |
| Dispersibility | ◯ | ◯ | ◯ | Δ | ◯ | X |

It can be understood from Table 1 that, in Test Examples 3 to 6 using a hydrocarbon volatile oil: isododecane, Test Examples 3, 4, and 6 using the waxes other than rice wax are poor in dispersibility or stability in volatilization. It also can be understood that, when rice wax is used, any example using a volatile hydrocarbon oil and/or a volatile silicone oil (Test Examples 1, 2, and 5) has a good stability.

Test Examples 7 to 11

Lipliner Pencils

With the raw materials shown in Table 2, lipliner pencils were prepared by the method similar to the above-mentioned method.

Each of the obtained lipliner pencils of Test Examples 7 to 11 was evaluated for the long-lasting property after application and the smoothness during application according to the above-mentioned criteria. The result is shown in Table 2.

TABLE 2

| (Lipliner pencil) | Test Example 7 | Test Example 8 | Test Example 9 | Test Example 10 | Test Example 11 |
|---|---|---|---|---|---|
| Rice wax | 20 | 20 | 20 | 10 | 25 |
| Isododecane | — | 24 | — | 24 | 24 |
| Decamethylcyclopentasiloxane | 15 | 15 | 10 | 25 | 10 |
| Dimethylpolysiloxane*1 | 24 | — | 29 | — | — |
| Hydrogenated polyisobutene | 10 | 10 | 10 | 10 | 10 |
| Sorbitan sesquiisostearate | 1 | 1 | 1 | 1 | 1 |
| Mica | 10 | 10 | 10 | 10 | 10 |
| Coloring agents | 20 | 20 | 20 | 20 | 20 |
| Total (%) | 100 | 100 | 100 | 100 | 100 |
| Long-lasting property | ◯ | ◎ | Δ | Δ | ◎ |
| Smoothness | ◯ | ◎ | ◯ | ◎ | ◯ |

*1 Silicone KF56 (manufactured by Shin-Etsu Chemical Co., Ltd.)

Each of Test Examples 7 to 9 is an example wherein the amounts of isododecane and decamethylcyclopentasiloxane, which are volatile oils, are changed. As Test Example 9 includes a small amount of volatile oil (i.e., 10% by mass), it results in a poor long-lasting property. To the contrary, as each of Test Examples 7 and 8 includes the proper amount of volatile oils, it has a good long-lasting property. For the smoothness, Test Example 8 is the best. Each of Test Examples 10 and 11 is an example wherein the amount of rice wax is changed. As Test Example 10 includes a small amount of rice wax (i.e., 10% by mass), it is slightly poor in the long-lasting property and the formability. Test Example 11 includes 25% by mass of rice wax and is excellent in the long-lasting property, but the smoothness is slightly poorer than that of Test Example 8.

Hereinafter, the formulation examples of the pencil-form cosmetic composition of the present invention will described. It is to be understood that the present invention is not limited by these formulation and is specified by the scope of claims.

Formulation Example 1

Lip Pencil

| | |
|---|---|
| Rice wax | 20% by mass |
| Decamethylcyclopentasiloxane | 15 |
| Isododecane | 35 |
| Polyisobutene | 10 |
| Sorbitan sesquiisostearate | 1 |
| Coloring agent | 19 |

(Production Method)

The raw materials other than volatile oils were dissolved at 100° C. and mixed by stirring. Then, volatile oils were added thereto, and the mixture was mixed by stirring at 80° C. or more and filled in a container.

Formulation Example 2

Lipstick

| | |
|---|---|
| Rice wax | 15% by mass |
| Decamethylcyclopentasiloxane | 10 |
| Isododecane | 20 |
| Polyisobutene | 15 |
| Diphenylsiloxy phenyl trimethicone | 30 |
| Sorbitan sesquiisostearate | 1 |
| Coloring agent | 9 |

(Production Method)

The raw materials other than volatile oils were dissolved at 100° C. and mixed by stirring. Then, volatile oils were added thereto, and the mixture was mixed by stirring at 80° C. or more and filled in a container.

Formulation Example 3

Eyebrow Pencil

| | |
|---|---|
| Rice wax | 25% by mass |
| Decamethylcyclopentasiloxane | 10 |
| Isododecane | 35 |
| Polyisobutene | 10 |
| Sorbitan sesquiisostearate | 1 |
| Coloring agent | 19 |

(Production Method)

The raw materials other than volatile oils were dissolved at 100° C. and mixed by stirring. Then, volatile oils were added thereto, and the mixture was mixed by stirring at 80° C. or more and filled in a container.

What is claimed is:

1. A pencil core-shaped cosmetic composition comprising:
(a) 15 to 50% by mass of volatile oil;
(b) 5 to 25% by mass of heavy liquid isoparaffin; and
(c) 5 to 30% by mass of rice wax.

2. A cosmetic product, wherein the pencil core-shaped cosmetic composition according to claim 1 is contained in a mechanical pencil-shaped container which enables the pencil core-shaped cosmetic composition to advance.

* * * * *